(12) United States Patent
Moncany et al.

(10) Patent No.: US 7,078,516 B1
(45) Date of Patent: Jul. 18, 2006

(54) NUCLEOTIDE SEQUENCES DERIVED FROM THE GENOME OF RETROVIRUSES OF THE HIV-1, HIV-2 AND SIV TYPE, AND THEIR USES IN PARTICULAR FOR THE AMPLIFICATION OF THE GENOMES OF THESE RETROVIRUSES AND FOR THE IN VITRO DIAGNOSIS OF THE DISEASES DUE TO THESE VIRUSES

(75) Inventors: Maurice Moncany, Paris (FR); Luc Montagnier, Le Plessis-Robinson (FR)

(73) Assignees: Institut Pasteur, Paris (FR); Institut National de la Sante et de la Recherche Medicale, Paris (FR)

( * ) Notice: Subject to any disclaimer, the term of this patent is extended or adjusted under 35 U.S.C. 154(b) by 34 days.

(21) Appl. No.: 08/472,928

(22) Filed: Jun. 7, 1995

Related U.S. Application Data

(62) Division of application No. 08/160,465, filed on Dec. 2, 1993, now Pat. No. 5,688,637, which is a continuation of application No. 07/820,599, filed on Jan. 21, 1992, now abandoned.

(30) Foreign Application Priority Data

Jun. 2, 1989 (FR) .............................. 89 07354
Sep. 20, 1989 (FR) ............................. 89 12371

(51) Int. Cl.
C07H 21/04 (2006.01)

(52) U.S. Cl. ................................ 536/24.33; 424/188.1; 424/208.1

(58) Field of Classification Search .............. 536/24.33, 536/24.3; 424/188.1, 208.1; 435/5
See application file for complete search history.

(56) References Cited

U.S. PATENT DOCUMENTS

| | | | |
|---|---|---|---|
| 4,683,195 A | 7/1987 | Mullis et al. | |
| 4,839,288 A | 6/1989 | Montagnier et al. | |
| 5,008,185 A | 4/1991 | Bacus | |
| 5,051,496 A | 9/1991 | Alizon et al. | |
| 5,079,351 A | 1/1992 | Sninsky et al. | 536/27 |
| 5,176,995 A | 1/1993 | Sninsky et al. | 435/6 |
| 5,268,268 A | 12/1993 | Sninsky et al. | 435/6 |
| 5,389,512 A | 2/1995 | Kwok et al. | |
| 5,688,637 A * | 11/1997 | Moncany et al. | 435/6 |
| 5,786,177 A | 7/1998 | Moncany et al. | 435/69.3 |

FOREIGN PATENT DOCUMENTS

| | | |
|---|---|---|
| EP | 0 229 701 | 7/1987 |
| EP | 0 269 445 | 6/1988 |
| EP | 0 269 520 | 6/1988 |
| EP | 0 272 098 | 6/1988 |
| EP | 0 318 281 | 5/1989 |
| EP | 0 320 495 | 6/1989 |
| JP | 62-217161 | 9/1987 |
| JP | 63-294800 | 12/1988 |
| WO | WO 87/07300 | 12/1987 |
| WO | WO 87/07906 | 12/1987 |
| WO | WO 88/01302 | 2/1988 |
| WO | WO 88/05440 | 7/1988 |

OTHER PUBLICATIONS

Laurence, J., 1988, "Update: HIV:1 Gene Nomenclature", AIDS Res. Human Retrovir. 4:vii–viii.*
Gallo, R.C., et al., 1988, "HIV/HTLV gene nomenclature", Nature 333:514.*
Horsburgh, Jr., et al., "Duration Human Immunodeficiency Virus Infection Before Detection of Antibody," The Lancet, 2, 637–639 (1989).
Ou et al., "DNA Amplification for Direct Detection of HIV–1 in DNA of Peripheral Blood Mononuclear Cells," Science, 239, 295–297 (1988).
Rayfield et al., "Mixed Human Immunodeficiency Virus (HIV) Infection in an Individual: Demonstration of both HIV Type 1 and Type 2 Proviral Sequences by Using Polymerase Chain Reaction," The Journal of Infectious Diseases, 158, 6, 1170–1176 (1988).
Chakrabarti et al., "Sequence of simian immunodeficiency virus from macaque and its relationship to other human and simian retroviruses", Nature, vol. 328, pp. 543–547 (1987).
Guyader et al., "Genome organization and transactivation of the human immunodeficiency virus type 2", Nature, vol. 326, pp. 662–669 (1987).
Courqnaud et al., Biosis No. 37083316, "HIV2 identification through PCR," Jun. 4–9, 1999, p. 668, Section C, Conference Doc. C.660.
Korber et al., Biosis No. 37094484, "Comparison of new HIV–2 viral isolates by southern blot and PCR," Jun. 4–9, 1989, p. 1013, Section G, Conference Doc. No. W.G.P.22.
Rayfield et al., Biosis No. 37073639, "PCR subtyping of HIV infections exhibiting reactive serologic responses to HIV–1 and HIV–2," Jun. 4–9, 1989, p. 159, Section A, Conference Doc. No. Th.A.P.109.
Rayfield et al., 1988, J. Infect. Dis. 158:1170–1176.
Ou et al., 1988, Science 239:295–297.
Hart et al., 1988, The Lancet, Sep. 10, 596–599.
Wain–Hobson et al., 1985, Cell 40:9–17.
Guyader et al., 1987, Nature 326:662–669.
Chakrabarti et al., 1987, Nature 328:543–547.
Guatelli et al., Clin. Microbiol. Rev. 2:217–226.
Derwent abstract WPI Acc No.: 1987–1200158/198729— Equivalent for Japanese Patent JP 62–21671.
Derwent abstract WPI Acc. No.: 1988–149202/198822— Equivalent for Japanese Patent JP 63–294800.

* cited by examiner

Primary Examiner—Jeffrey S. Parkin
(74) Attorney, Agent, or Firm—Finnegan, Henderson, Farabow, Garrett & Dunner LLP

(57) ABSTRACT

The invention provides oligonucleotide primers selected from the group consisting of a nucleotide sequence of the gag, vpr, and pol genes of HIV-1 Bru, HIV-1 Mal, HIV-1 Eli, HIV-2 ROD, and SIV MAC; the nef, vif, and vpx genes of HIV-2 ROD and SIV MAC; and the env, nef, vif, and vpu genes of HIV-1 Bru, HIV-1 Mal and HIV-1 Eli and nucleotide sequences complementary thereto.

3 Claims, No Drawings

```
                          SEQUENCE LISTING (1) GENERAL INFORMATION:

(iii) NUMBER OF SEQUENCES: 68

(2) INFORMATION FOR SEQ ID NO:1:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:1:

TGGCGCCCGA ACAGGGAC                                                  18

(2) INFORMATION FOR SEQ ID NO:2:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:2:

TGGCGCCTGA ACAGGGAC                                                  18

(2) INFORMATION FOR SEQ ID NO:3:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:3:

GGCCAGGGGG AAAGAAAAA                                                 19

(2) INFORMATION FOR SEQ ID NO:4:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:4:

GGCCCGGCGG AAAGAAAAA                                                 19

(2) INFORMATION FOR SEQ ID NO:5:
```

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GGCCAGGAGG AAAGAAAAA                                                     19

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

TGCCCATACA AAATGTTTTA                                                    20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TGCCCACACT ATATGTTTTA                                                    20

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

TGCATGGCTG CTTGATG                                                       17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

TGCATAGCTG CCTGGTG                                                       17

(2) INFORMATION FOR SEQ ID NO:10:

(i) SEQUENCE CHARACTERISTICS:
        (A) LENGTH: 20 base pairs
        (B) TYPE: nucleic acid
```

```
    (C) STRANDEDNESS: single
    (D) TOPOLOGY: linear (ii) MOLECULE TYPE: DNA (genomic)

(xi) SEQUENCE DESCRIPTION: SEQ ID NO:10:
```

CTTTGCATGG CTGCTTGATG                                            20

(2) INFORMATION FOR SEQ ID NO:11:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:
```

CTCTGCATAG CTGCCTGGTG                                            20

(2) INFORMATION FOR SEQ ID NO:12:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:
```

CATCAAGCAG CCATGCAAAG                                            20

(2) INFORMATION FOR SEQ ID NO:13:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:
```

CACCAGGCAG CTATGCAGAG                                            20

(2) INFORMATION FOR SEQ ID NO:14:

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:
```

AGGGCTGTTG GAAATGTGG                                             19

(2) INFORMATION FOR SEQ ID NO:15:

```
    (i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:15:

AGGGCTGTTG GAAAGGTGG                                                      19

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CCACATTTCC AGCATCCCT                                                      19

(2) INFORMATION FOR SEQ ID NO:17:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CCACATTTCC AGCAGCCCT                                                      19

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CCACATTTCC AGCACCCCT                                                      19

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GATAGATGGA ACAAGCCCCA G                                                   21

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

TCCATTTCTT GCTCTCCTCT GT                                                  22

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TAAAGCCAGG AATGGATGGC CCAA                                    24

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

TAAAGCCAGG AATGGATGGA CCAA                                    24

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

TTGGGCCATC CATTCCTGGC TTTA                                    24

(2) INFORMATION FOR SEQ ID NO:24:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

TTGGTCCATC CATTCCTGGC TTTA                                    24

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

TGGACTGTCA ATGACATACA GAA                                     23

(2) INFORMATION FOR SEQ ID NO:26:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

TGGACTGTCA ATGATATACA GAA                                              23

(2) INFORMATION FOR SEQ ID NO:27:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

TTCTGTATGT CATTGACAGT CCA                                              23

(2) INFORMATION FOR SEQ ID NO:28:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

TTCTGTATGT CATTGACTGT CCA                                              23

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CATGGGTACC AGCACACAAA GG                                               22

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

CCTTTGTGTG CTGGTACCCA TG                                               22

(2) INFORMATION FOR SEQ ID NO:31:

(i) SEQUENCE CHARACTERISTICS:
        (A) LENGTH: 20 base pairs
        (B) TYPE: nucleic acid
        (C) STRANDEDNESS: single

```
            (D) TOPOLOGY: linear (ii) MOLECULE TYPE: DNA (genomic)

(xi) SEQUENCE DESCRIPTION: SEQ ID NO:31:

TGGAAAGGTG AAGGGGCAGT                                              20

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:32:

TGGAAAGGTG AAGGAGCAGT                                              20

(2) INFORMATION FOR SEQ ID NO:33:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:33:

ACTGCCCCTT CACCTTTCCA                                              20

(2) INFORMATION FOR SEQ ID NO:34:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:34:

ACTGCCCCTT CTCCTTTCCA                                              20

(2) INFORMATION FOR SEQ ID NO:35:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:35:

ACTGCCCCTT CCCCTTTCCA                                              20

(2) INFORMATION FOR SEQ ID NO:36:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: DNA (genomic)
```

(xi) SEQUENCE DESCRIPTION: SEQ ID NO:36:

AGAGACTCTT GCGGGCGCGT G                                      21

(2) INFORMATION FOR SEQ ID NO:37:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

ATATACTTAG AAAAGGAAGA AGG                                    23

(2) INFORMATION FOR SEQ ID NO:38:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

CCTTCTTCCT TTTCTAAGTA TAT                                    23

(2) INFORMATION FOR SEQ ID NO:39:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

AGCTGAGACA GCAGGGACTT TCCA                                   24

(2) INFORMATION FOR SEQ ID NO:40:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

TATGGAGGAG GAAAAGAGAT GGATAGT                                27

(2) INFORMATION FOR SEQ ID NO:41:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:41:

TAGCACTTAT TTCCCTTGCT TT                                     22

(2) INFORMATION FOR SEQ ID NO:42:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:42:

AAAGCAAGGG AAATAAGTGC TA                                              22

(2) INFORMATION FOR SEQ ID NO:43:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:43:

CCCTTGTTCA TCATGCCAGT AT                                              22

(2) INFORMATION FOR SEQ ID NO:44:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

ATGTCAGATC CCAGGGAGA                                                  19

(2) INFORMATION FOR SEQ ID NO:45:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

CCTGGAGGGG GAGGAGGAGG A                                               21

(2) INFORMATION FOR SEQ ID NO:46:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

CCAATTCCCA TACATTATTG TGCCCC                                          26

(2) INFORMATION FOR SEQ ID NO:47:

(i) SEQUENCE CHARACTERISTICS:

```
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

GGGGCACAAT AATGTATGGG AATTGG                                         26

(2) INFORMATION FOR SEQ ID NO:48:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

AATGGCAGTC TAGCAGAAGA AGA                                            23

(2) INFORMATION FOR SEQ ID NO:49:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

ATCCTCAGGA GGGGACCCAG AAATT                                          25

(2) INFORMATION FOR SEQ ID NO:50:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

AATTTCTGGG TCCCCTCCTG AGGAT                                          25

(2) INFORMATION FOR SEQ ID NO:51:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

GTGCTTCCTG CTGCTCCCAA GAACCC                                         26

(2) INFORMATION FOR SEQ ID NO:52:

(i) SEQUENCE CHARACTERISTICS:
        (A) LENGTH: 26 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:52:

GGGTTCTTGG GAGCAGCAGG AAGCAC                                                    26

(2) INFORMATION FOR SEQ ID NO:53:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:53:

ATGGGTGGCA AGTGGTCAAA AAGTAG                                                    26

(2) INFORMATION FOR SEQ ID NO:54:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:54:

CTACTTTTTG ACCACTTGCC ACCCAT                                                    26

(2) INFORMATION FOR SEQ ID NO:55:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:55:

TATTAACAAG AGATGGTGG                                                            19

(2) INFORMATION FOR SEQ ID NO:56:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:56:

CCAGCAAGAA AAGAATGAA                                                            19

(2) INFORMATION FOR SEQ ID NO:57:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:57:

```
TTCATTCTTT TCTTGCTGG                                                    19

(2) INFORMATION FOR SEQ ID NO:58:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:58:

AAAAGAAAAG GGGGGACTGG A                                                 21

(2) INFORMATION FOR SEQ ID NO:59:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:59:

TCCAGTCCCC CCTTTTCTTT T                                                 21

(2) INFORMATION FOR SEQ ID NO:60:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:60:

AAAGTCCCCA GCGGAAAGTC CC                                                22

(2) INFORMATION FOR SEQ ID NO:61:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:61:

GATTATGGAA AACAGATGGC AGGTGAT                                           27

(2) INFORMATION FOR SEQ ID NO:62:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

GCAGACCAAC TAATTCATCT GTA                                               23
```

(2) INFORMATION FOR SEQ ID NO:63:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

TACAGATGAA TTAGTTGGTC TGC                                  23

(2) INFORMATION FOR SEQ ID NO:64:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

CTTAAGCTCC TCTAAAAGCT CTA                                  23

(2) INFORMATION FOR SEQ ID NO:65:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

GTAAGTAGTA CATGTAATGC AACCT                                25

(2) INFORMATION FOR SEQ ID NO:66:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:66:

AGCAGAAGAC AGTGGCCATG AGAG                                 24

(2) INFORMATION FOR SEQ ID NO:67:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:67:

ACTACAGATC ATCAATATCC CAA                                  23

(2) INFORMATION FOR SEQ ID NO:68:

(i) SEQUENCE CHARACTERISTICS:
        (A) LENGTH: 26 base pairs

-continued

```
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:68:

ATGGGTGGCA AATGGTCAAA AAGTAG                                          26
```

NUCLEOTIDE SEQUENCES DERIVED FROM THE GENOME OF RETROVIRUSES OF THE HIV-1, HIV-2 AND SIV TYPE, AND THEIR USES IN PARTICULAR FOR THE AMPLIFICATION OF THE GENOMES OF THESE RETROVIRUSES AND FOR THE IN VITRO DIAGNOSIS OF THE DISEASES DUE TO THESE VIRUSES

This application is a divisional of U.S. application No. 08/160,465, filed 02 Dec. 1993, now U.S. Pat. No. 5,688,637, which is a continuation of U.S. application No. 07/820,599, now abandoned.

The present invention relates to oligonucleotide sequences which can be used for the implementation of techniques for the amplification of specific nucleotide sequences of human immunodeficiency retroviruses of the HIV type or of monkey immunodeficiency retroviruses of the SIV type.

The invention relates in particular to the use of such sequences for methods of in vitro diagnosis in man of the infection of an individual by a retrovius of the HIV type (at present HIV-1 and/or HIV-2).

The isolation and characterization of retroviruses grouped together under the designations HIV-1 and HIV-2 were described in the European patent applications No. 85/905.513.9 and No. 87/400.151.4, respectively. These retroviruses were isolated from several patients exhibiting symptoms of a lymphadenopathy or an Acquired Immunodeficiency Syndrome (AIDS).

The retroviruses of the HIV-2 type like the retroviruses of the HIV-1 type are characterized by a tropism for the human T4 lymphoctyes and by a cytopathogenic effect with regard to these lymphocytes when they multiply within them to give rise to, among other things, generalized and persistent polyadenopathies, or an AIDS.

Another retrovirus, designated SIV-1, this designation replacing the earlier one STLV-III, was isolated from the rhesus macaque monkey (M. D. DANIEL et al. Science, 228, 1201 (1985); N. L. LETWIN et al., Science, 230, 71 (1985) under the designation "SLTV-IIImac").

Another retrovirus, designated "STLV-III$_{AGM}$" (or SIV$_{AGM}$), was isolated from wild green monkeys. However, in contrast to the viruses present in the rhesus macaque monkey, the presence of STLV-III$_{AGM}$ does not appear to induce a disease of the AIDS type in the African green monkey.

For reasons of semantics, these virus s will be designated in what follows only by the expression SIV (the expression SIV is an English abbreviation for "Simian Immunodeficiency Virus", possibly followed by an abbreviation designating the species of monkey from which they are derived, for example, "MAC" for "macaque" or "AGM" for the "African Green Monkey".

A strain of the retrovirus SIV-1Mac was deposited with the C.N.C.M. on 7 Feb. 1986 under the No. I-521.

The continuation of the study of the retroviruses HIV-1 and HIV-2 has also led to the production of DNA sequences (cDNA) complementary to the RNAs of their genome. The complete nucleotide sequence of a cDNA of a retrovirus representative of the HIV-2 class (HIV-2 ROD) was deposited on 21/02/1986 with the C.N.C.M. under the No. I-522, under the reference name LAV-2 ROD.

Similarly, the complete nucleotide sequence of a cDNA of a retrovirus representative of the HIV-1 class is described by WAIN—HOBSON, SONIGO, COLE, DANOS and ALIZON in CE11 (January 1985).

Also for semantic reasons, and the viruses of the HIV-1 and HIV-2 type will sometimes be designated in the subsequent description by the expression HIV.

The methods for the in vitro diagnosis of the infections by viruses of the HIV-1 or HIV-2 type currently practised, are based on the detection of anti-HIV-1 or anti-HIV-2 antibodies possibly present in a biological sample (biopsy) or in a biological fluid, for example in a serum obtained from the patient under study, by placing this biological fluid in contact with extracts or antigens of HIV-1 or HIV-2 under conditions which could give rise to the production of an immunological reaction between these extracts or antigens and these antibodies.

There is the risk that such diagnostic methods will give rise to false negatives, in particular in the case of a recent infection of an individual by the viruses of the HIV type.

The techniques of gene amplification make a considerable 7 contribution to the development of in vitro diagnostic methods which are particularly sensitive for viral diseases. Among these techniques of gene amplification, menti n may be made of the PCR (Polymerase Chain Reaction) technique as described in the European patent applications No. 86/302.298.4 of 27/03/1986 and No. 87/300.203.4 of 09/01/1987, or also the technique known as "Qβreplicase" described in Biotechnology, vol. 6 page 1197 (October 1988) and that which makes use of a RNA polymerase (T7RNA polymerase) described in the International patent application No. WO89/01050. These techniques make it possible to improve the sensitivity of detection of the nucleic acids of the virus, and require the use of specific primers for synthesis.

In the case of research on the viruses of the HIV type, the choice of primers is problematical. In fact, owing to the great variability of the nucleotide sequences of the viral genome, a primer corresponding to the known sequence of a given isolate of a virus of the HIV type may fail in the amplification of certain viral variants of the HIV type. Furthermore, even if a primer is selected from a region of the genome which is conserved from one HIV virus to another, its "efficiency" is not thereby insured and may give rise to poor amplification yields.

The precise objective of the present invention is to provide oligonucleotide primers which, inter alia, make possible the amplification of the genome of all viruses of the HIV and SIV types, in particular for diagnostic purposes, with yields considered to be maximal in the present state of the art and which, in particular, do not given rise to the presence of many aspecific bands.

The primers of the present invention are specific both for the viruses of the HIV-1 groups and/or the viruses of the HIV-2 and SIV groups, and are insensitive to variations of the genome of these viruses.

The object of the present invention is oligonucleotide primers of about 15 to 30 nucleotides which can be used the genomic amplification of the viruses of the HIV-I type and/or HIV-2 and SIV types.

The invention relates to any nucleotide sequence characterized in that its sequence:

is either selected from those which are contained in one of the nucleotide sequences included in the gag, vpr and p 1 genes of the virus s HIV-1 Bru, HIV-1 Mal, HIV-1 Eli, HIV-2 ROD and SIV MAC, or in the nef, vif and vpx genes of the viruses HIV-2 ROD and SIV MAC, or in the env, nef, vif and vpr genes of the viruses HIV-1 Bru, HIV-1 Mal and HIV-1 Eli, and more particularly from those which are contained in the nucleotide sequences defined hereafter, or (particularly in the case of the longest sequences) contains one of the above-mentioned nucleotide sequences derived from HIV-1 Bru or HIV-1 Mal, or HIV-1 Eli or HIV-2 ROD or SIVMac, or contains a complementary nucleotide sequence of one of these latter sequences, it being understood that the possible additional nucleotides which "extend beyond" the nucleotide sequence of the type in question at the 3' and 5' ends preferably coincide with those which are placed external to the 5' or 3' end of the same sequence within the complete sequence of the viruses of the HIV-1, HIV-2 or SIV MAC type mentioned above, or, if this nucleotide sequence is not identical with one of the above-mentioned nucleotide sequences, or is not complementary to one of these sequences, it is nonetheless capable of hybridizing with a nucleotide sequence derived from the viruses HIV-1 Bru, HIV-1 Mal, HIV-1 Eli and/or with a nucleotide sequence derived from the viruses HIV-2 ROD or SIV MAC mentioned above. The hybridization may be carried out at a temperature of 60° C.±1° C. (preferably 60° C.±0.5° C.), recommended for an optical yield.

The numbering of the nucleotides mentioned below corresponds to that used in the reference manual "Human Retrovirus and AIDS-1989" edited by the "Los Alamos National Laboratory—New Mexico—USA".

(The sequences of the viruses HIV-1 Mal, HIV-1 Eli were described by MONTAGNIER, SONIGO, WAIN-HOBSON and ALIZON in the European patent application No. 86.401380 of 23/06/86).

The sequences of the invention are synthesized in a synthesizer marketed by Applied Biosystems (phosphoroamidite method) or in any other apparatus employing a similar method.

The invention relates more particularly to the oligonucleotide sequences characterized by the following nucleotide sequences (shown in the 5'→3' sense; the initials "S" and "AS" indicate whether the oligonucleotide is sense or antisense, i.e. whether the oligonucleotide is oriented in the 5'→3' or in the 3'→5' sense): 1°) sequences common the genomes of the HIV-1, HIV-2 and SIV viruses (the pairs of numbers separated by a dash indicate the position of the nucleotides in the genomes corresponding respectively to the virus HIV-1 Bru, HIV-1 Mal, HIV-1 Eli, HIV-2 ROD and SIV):

specific sequences of the gag gene of the genome of the above-mentioned viruses (gene coding for a group of antigens specific for the nucleotide of these viruses).

Certain variants may be introduced by certain positions of the nucleotide sequences indicated below, without effecting the hybridization properties of these nucleotide sequences with the genes of the viruses of the HIV and/or SIV types. The nucleotide sequences containing these variants are shown below the original nucleotide sequences from which they are derived by substitution of one or more bases. The bases representing modifications of the initial nucleotide sequences are indicated by a letter directly beneath the base which they replace in the initial sequences; whereas the bases of the original sequences which are not replaced in the sequences bearing these variants are shown by dots.

The synthesis of the primers is carried out by using all of the variants simultaneously. It is the mixture of all of the variants for a given sequence which is used in the tests.

MMy1 : TGG CGC CCG AAC AGG GAC (SEQ ID NO:1) ... ... .T. ... ... ... (SEQ ID NO:2) S, 636-653, 635-652, 636-653, 859-876, 834-851

MMy2 : GGC CAG GGG GAA AGA AAA A (SEQ ID NO:3) ... .C. .C. ... ... ... . (SEQ ID NO:4) ... ... . A. ... ... ... . (SEQ ID NO:5) S,854-872,863-888,848-872, 1160-1184, 1124-1148

MMy3 : TGC CCA TAC AAA ATG TTT TA (SEQ ID NO:6) ... ... C.. T.T ... ... . (SEQ ID NO:7) AS, 990-881, 916-897,900-881,1212-1193,1176-1157 MMy4 : TGC ATG GCT GCT TGA TG (SEQ ID NO:8) ... ..A ... ..C .. G .. (SEQ ID NO:9) AS,1385-1369,1419-1403,1385-1369,1703-1687,1667-1651

MMy4B : CTT TGC ATG GCT GCT TGA TG (SEQ ID NO:10) ..c ... ..A ... ..C ..G .. (SEQ ID NO:11). AS, 1388-1369, 1421-1403, 1388-1369, 1706-1687, 1670-1651,

MMy4Ba : CAT CAA GCA GCC ATG CAA AG (SEQ ID NO:12) ..C ..G ... ..T ... ..G .. (SEQ ID NO:13) S, 1369-1388, 1403-1421, 1369-1388, 1687-1706, 1651-1670,

MMy28 : AGG GCT GTT GGA AAT GTG G (SEQ ID NO:14) ... ... ... ... .G ... . (SEQ ID NO:15) S, 2021-2039, 2055-2073, 2024-2042, 2329-2349, 2299-2318,

MMy28a : CCA CAT TTC CAG CAT CCC T (SEQ ID NO:16) ... ... ... ... ..G ... . (SEQ ID NO:17) ... ... ... ... .. C ... . (SEQ ID NO:18) AS, 2039-2021, 2073-2055, 2042-2024, 2349-2329, 2318-2299 specific sequences of thevpr gene:

MMy18 : GAT AGA TGG AAC AAG CCC CAG (SEQ ID NO:19) S, 5590-5610, 5585-5605, 5554-5574, 6233-6296, 6147-6170,

MMy19 : TCC ATT TCT TGC TCT CCT CTG T (SEQ ID NO:20) AS, 5870-5849, 5865-5844, 5834-5813, 6551-6531, 6454-6431, specific sequences of the pol gene:

MMY29 : TAA AGC CAG GAA TGG ATG GCC CAA (SEQ ID NO:21) ... ... ... ... ... ... .A. ... (SEQ ID NO:22) S, 2620-2643, 2615-2638, 2584-2607, 2971-2994, 2887-3010

MMy29a : TTG GGC CAT CCA TTC CTG GCT TTA (SEQ ID NO:23) ... .T. ... ... ... ... ... (SEQ ID NO:24) AS, 2643-2620, 2638-2615, 2607-2384, 2994-2971, 3010-2887,

MMy30 : TGG ACT GTC AAT GAC ATA CAG AA (SEQ ID NO:25) ... ... ... ... ..T ... ... .. (SEQ ID NO:26) S, 3339-3361, 3334-3356, 3303-3325, 3690-3712, 3606-3628,

MMy30a : TTC TGT ATG TCA TTG ACA GTC CA (SEQ ID NO:27) ... ... ... ... ... ..T ... .. (SEQ ID NO:28) AS, 3361-3339, 3356-3334, 3325-3303, 3712-3690, 3628-3606,

MMy31 : CAT GGG TAC CAG CAC ACA AAG G (SEQ ID NO:29) S, 4186-4207, 4181-4202, 4150-4171, 4534-4555, 4450-4471,

MMy31a : CCT TTG TGT GCT GGT ACC CAT G (SEQ ID NO:30) AS, 4207-4186, 4202-4181, 4171-4150, 4555-4534, 4471-4450,

MMy32 : TGG AAA GGT GAA GGG GCA GT (SEQ ID NO:31) ... ... ... ... ..A ... .. (SEQ ID NO:32) S, 4992-5011, 4987-5006, 4956-4975, 5340-5359, 52561 -5275,

MMy32 : ACT GCC CCT TCA CCT TTC CA (SEQ ID NO:33) ... ... ... ..T ... ... .. (SEQ ID NO:34) ... ... ... .. C ... ... .. (SEQ ID NO:35) AS, 5011-4992, 5006-4987, 4975-4956, 5359-5340, 5275-5256

2°) sequences common to the genomes of the HIV-2 and SIV viruses (the pairs of numbers separated by a dash indicate the position of the nucleotides in the genomes corresponding to the viruses HIV-2 ROD and SIV-MAC, respectively).

specific sequences of the nef of HIV-2 ROD and SIV MAC gene (coding for a negative factor of 27 kD)

MMy12 : AGA GAC TCT TGC GGG CGC GTG (SEQ ID NO:36) S, 9165-9185, 9139-9159,

MMy13 : ATA TAC TTA GAA AAG GAA GAA GG (SEQ ID NO:37) S, 9542-9564, 9516-9538,

MMy13bis : CT TCT TCC TTT TCT AAG TAT AT (SEQ ID NO:38) AS, 9564-9542, 9538-9516, MMy14 : AGC TGA GAC AGC AGG GAC TTT CCA (SEQ ID NO:39) AS, 9956-9933, 9893-9870,
specific sequences of the vif HIV-2ORD and SIV MAC gene (coding for an infectivity fator of 23 kD)
MMy20 : TAT GGA GGA GGA AAA GAG ATG GAT AGT (SEQ ID NO:40) S, 5424-540, 5340-5366,
MMy21 : TAG CAC TTA TTT CCC TTG CTT T (SEQ ID NO:41) S, 5754-5775, 5670-5691,
MMy21bis : AAA GCA AGG GAA ATA AGT GCT A (SEQ ID NO:42) AS, 5775-5754, 5691-5670.
MMy22 : CCC TTG TTC ATC ATG CCA GTA T (SEQ ID NO:43) AS, 6082-6061, 5995-5974,
specific sequences of the vpx gene (coding for a protein of 12 kD)
MMy23 : ATG TCA GAT CCC AGG GAG A (SEQ ID NO:44) S, 5900-5918, 5813-5831,
MMy24 : CCT GGA GGG GGA GGA GGA GGA (SEQ ID NO:45) AS, 6228-6208, 6141-6121,
3°) Sequences common to the genomes of the viruses HIV-1 Bru, HIV-1 Mal and HIV-1 Eli (the pairs of numbers separated by a dash indicate the position of the nucleotides in the genomes corresponding to the viruses HIV-1 Bru, HIV-1 Mal and HIV-1 Eli, respectively).
specific sequences of the env gene (coding for the envelope proteins)
MMy5 : CCA ATT CCC ATA CAT TAT TGT GCC CC (SEQ ID NO:46) S, 6905-6930,6903-628,6860-6885
MMy5 : GGG GCA CAA TAA TGT ATG GGA ATT GG (SEQ ID NO:47) AS, 6930-6905, 6928-6903, 6885-6860,
MMy6 : AAT GGC AGT CTA GCA GAA GAA GA (SEQ ID NO:48) S,7055-7077, 7053-7075, 7010-7032
MMy7 : ATC CTC AGG AGG GGA CCC AGA AAT T (SEQ ID NO:49) S, 7360-7384, 7349-7373,7306-7330
MMy7a : AAT TTC TGG GTC CCC TCC TGA GGA T (SEQ ID NO:50) AS, 7384-7360,7373-7349,7330-7306
MMy8 : GTG CTT CCT GCT GCT CCC AAG AAC CC (SEQ ID NO:51) AS, 7857-7832,7846-7821,7800-7775
MMy8a : GGG TTC TTG GGA GCA GCA GGA AGC AC (SEQ ID NO:52) S, 7832-7857, 7821-7846, 7775-7800,
MMy9 : ATG GGT GGC AAG TGG TCA AAA AGT AG (SEQ ID NO:53) ... ... ... ..A ... ... ... ... (SEQ ID NO:68) S,8844-8869, 8836-8861, 8787-8812,
MMy9a : CTA CTT TTT GAC CAC TTG CCA CCC AT (SEQ ID NO:54) AS, 8869-8844, 8861-8836, 8812-8787,
MMy78 : TAT TAA CAA GAG ATG GTG G (SEQ ID NO:55) S, 7629-7647, 7612-7630, 7572-7590,
MMy89 : CCA GCA AGA AAA GAA TGA A (SEQ ID NO:56) S, 8224-8242, 8213-8231, 8167-8185,
MMy89 a : TTC ATT CTT TTC TTG CTG G (SEQ ID NO:57) AS, 8242-8224, 8231-8213, 8185-8167,
specific sequences of the nef of HIV-1 Bru, HIV-1 Mal, and HIV-1 gene: MMy10 : AAA AGA AAA GGG ACT GGA (SEQ ID NO:58) S, 9116-9136, 9117-9137, 9062-9082,
MMy10a : TCC AGT CCC CCC TTT TCT TTT (SEQ ID NO:59) AS, 9136-9116, 9137-9117, 9082-9062,
MMy11 : AAA GTC CCC AGC GGA AAG TCC C (SEQ ID NO:60) AS,9503-9483, 9505-9484, 9449-9428,
specific sequences of the vif of HIV-1 Bru, HIV-1 Mal, and HIV-1 Eli gene
MMy15 : GAT TAT GGA AAA CAG ATG GCA GGT GAT (SEQ ID NO:61) S, 5073-5099, 5068-5094, 5037-5063,
MMy16 : GCA GAC CAA CTA ATT CAT CTG TA (SEQ ID NO:62) S, 5383-5405, 5378-5400, 5347-5369,
MMy16a : TAC AGA TGA ATT AGT TGG TCT GC (SEQ ID NO:63) AS, 5405-5383, 5400-5378, 5369-5347,
MMy17 : CTT AAG CTC CTC TAA AAG CTC TA (SEQ ID NO:64) AS, 5675-5653, 5670-5648, 5639-5617,
specific sequences of the vpu gene
MMy25 : GTA AGT AGT ACA TGT AAT GCA ACC T (SEQ ID NO:65) S, 6081-6105, 6076-6100, 6045-6069,
MMy26 : AGC AGA AGA CAG TGG CCA TGA GAG (SEQ ID NO:66) S, 6240-6263, 6238-6261, 6207-6230,
MMy27 : ACT ACA GAT CAT CAA TAT CCC AA (SEQ ID NO:67) AS, 6343-6321, 6338-6316, 6307-6285, The object of the invention is also the sequences (or primers possessing a complementary nucleotide structure to those of the primers defined above.

It also relates to the nucleotide sequences possessing certain mutations with respect to those defined above without the hybridization properties, such as defined above, of these sequences being modified. The percentage of nucleotides different from those constituting the sequences described above without thereby affecting the hybridization properties of the sequences of the invention may attain 40%.

Generally speaking, in the case of a sense (S) primer, a larger number of mutations is tolerated at the 5' end than at the 3' end of the primer, the 3' end being required to hybridize perfectly with a specific strand of a nucleotide sequence in order for this sequence to be amplified. In the case of an anti-sense (AS) primer, it is at the 3' end that tolerance is allowed.

The object of the invention is also the primers such as those defined above and including a conserved stretch of at least 5 bases on either side of the central part which contains modifications without the above hybridization properties being modified.

One of the characteristics of the oligonucleotide primers of the invention is that of giving a clear-cut amplification band, usually free of aspecific bands when the technical directions for use described in the present invention are followed. This fact is due to the length of the primers which may attain 27 bases and thus increases the specificity of hybridization, as well as to the drastic conditions of use which make it possible to eliminate parasitic combinations. In addition to the percentage of homology with the reference matrix, the specificity for each type of virus is a function of the length of the primer which may attain as many as 40 bases in order to obtain an acceptable yield.

The invention also includes primers such as those described above linked at their 5' end to a promoter for the implementation of a method of genomic amplification by the synthesis of multiple copies of DNA or RNA such as that described in the European patent application No. 88/307.102.9 of 01/08/1988.

The object of the invention is in particular the use of the primers described above for the implementation of a procedure of gene amplification of nucleotide sequences of the viruses of the HIV-1 and/or HIV-2 and/or SIV type, this produce being applicable to the in vitro diagnosis of the potential infection of an individual by a virus of the HIV-1 and/or HIV-2 type or of an animal by at least one of the three viruses (HIV-1, HIV-2, SIV).

This method of in vitro diagnosis of the invention is carried out starting from a biological sample same (for example of biological fluid such as serum, the lymphocytes of circulating blood) obtained from a patient under study, and comprising mainly the following steps:

a step involving the extraction of the nucleic acid to be detected belonging to the genome of the virus of the HIV-1 and/or HIV-2 and/or SIV type possibly present in the above-mentioned biological sample and, where appropriate, a step involving the incubation of the said nucleic acid with a reverse transcriptase if this latter is in the form of RNA in order to obtain a double-stranded nucleic acid (this last step being also designated below as the step of retrotranscription of the viral RNA).

a cycle comprising the following steps:

denaturation of the double-stranded nucleic acid to be detected, which leads to the formation of a single stranded nucleic acid, hybridization of each of the strands of the nucleic acid obtained during the previous denaturation step with at least one primer according to the invention, by placing the strands mentioned above with at least one primer couple according to the invention under the conditions of hybridization defined below, formation, starting from the primers, of the DNA complementary to the strands to which they are hybridized in the presence of a polymerization agent (DNA polymerase) and the four different nucleoside triphosphates (DNTP) which leads to the formation of a greater number of double-stranded nucleic acids to be detected than in the previous denaturation step, this cycle being repeated to defined number of times in order to obtain the said nucleic acid sequence to be detected possibly present in the biological sample in an amount sufficient to allow its detection, a step involving the detection of the possible presence of the nucleic acid belonging to the genome of the virus of the HIV-1 and/or HIV-2 and/or SIV type in the biological sample.

The hybridization step described above is advantageously performed at 60° C. for 1 minute 30 seconds in the "10 X buffer", the composition of which (expressed as final concentrations for use) is indicated below.

The method of in vitro diagnosis of the invention may be carried out either starting from the viral RNA, or from the episomal or integrated complementary DNA.

In fact, the genomes of the HIV and SIV viruses exist in the form of RNA or DNA, depending on the localization of the virus in the organism.

When the virus is situated within the cells of the organism, in particular in the interior of blood cells, its RNA is recopied into DNA by a reverse transcriptase. On the other hand, the genome of the viruses of the HIV type in the extracellular medium, in particular in the blood, remains in the RNA form.

The extraction step according to the invention of the viral DNA contained in the cells of the biological sample recommended by the inventors—in addition to the standard method using phenol/chloroform—comprises the following steps:

suspension of the cell pellet in 0.5 ml of boiled water in a Potter homogenizer with a wide pestle, grinding of the cells by "forwards and backwards rotation", addition of Triton X100 to give a give a final concentration of 0.1%, heat denaturation for 15 to 25 minutes at 100° C., brief centrifugation in order to remove only the cell debris, precipitation of the DNA overnight at −20° C. by addition of 2.5 volumes of absolute ethanol and 10% of the final volume of 3 molar sodium acetate. The DNA is subsequently recovered, then resuspended in boiled water after having been washed twice with 70° ethanol. It should be noted that this method leads to the simultaneous precipitation of the DNAs and the RNAs which make possible the detection of the genomic message of the viruses of the HIV or SIV types by use of the method called "direct PCR-DNA" or by that called "PCR-RNA".

The step involving the extraction of the viral RNA is usually performed in the classical manner well-known to the person skilled in the art.

After extraction of the RNA, it is necessary to carry out an additional step involving the transformation of the single-stranded RNA into double-stranded DNA when the in vitro diagnosis of the invention is performed on biological samples containing the viruses of the HIV-1 and/or HIV-2 and/or SIV types, the genomes of which are in the RNA form.

This transformation of the RNA into DNA is carried out by treatment of the RNA obtained after extraction of the biological sample, in particular serum, with a reverse transcriptase in a suitable medium.

The object of the invention more particularly among other things is a method of in vitro diagnosis such as that defined above in which the step of retrotranscription of viral RNA is carried out in the following manner:

10 µg of RNA, extracted and resuspended in water, is placed in the presence of the primer couple at a concentration of 40 µM of each in a final volume of 40 µl. The mixture is denatured at 100° C. for 10 minutes, then plunged into ice-cold water, 10 µl of the following mixture are added: 5 µl of the "10 X buffer" described below +1 unit of AMV (Avian Myeloblastosis Virus) or MuMLV (Moloney Leukemia Virus) reverse transcriptase +1 unit of Taq-polymerase +1 µl of a 25 mM mixture of each of the 4 dNTP+water as required to give 10 µl. The final volume is thus 50 µl.

This reaction is carried out in two steps:
a) 1st step: synthesis of the cDNA by the action of the reverse transcriptase at 42° C. for 13 minutes,
b) 2nd step: standard gene amplification: the mixture is heated at 95° C. for 3 minutes to destroy the reverse transcriptase and to carry out the dehybridization/hybridization step, then the cycle previously described for gene amplification is initiated.

The object of the invention is more particularly a method of in vitro diagnosis such as that described above in which the denaturation step is performed in the presence of one or several primer couples of the invention. In fact, as has been specified above, one of the characteristics of the oligonucleotides (or primers) of the invention is that they give a clear-cut amplification band, usually free of aspecific bands, when they are used under the following conditions:

hybridization: the primers (1 µl of a 40 µmolar (40 µM) solution of each primer) are placed in the presence of the matrix DNA (100 to 300 ng) for the first step of denaturation-reassociation; the tubes containing this mixture of matrix DNA and primers is heated for 10 minutes at 100° C., then plunged into ice-cold water in order to increase the extent of matrix DNA/primer reassociation. The primers must be used at a final concentration of 0.8 µM each in the amplification step which follows.

amplification: the 4 dNTPs are added to the preceding mixture, each being used at a concentration of 0.5 µmolar in the final solution (50 µl), and one unit of Taq-polymerase per 50 µl of reaction mixture; this step is carried out in an amplification buffer of the present invention, usually designated by the name "10 X buffer", the composition of which (when it is diluted 1/10) is the following: Tris-HCl, pH 8.9: 50 mM; $(NH_4)_2SO_4$: 15 mM; $MgCl_2$: 5 mM; β-mercaptoethanol: 10 mM; gelatin: 0.25 mg/ml. 5 µl this buffer and water to give 50 µl are added to the preceding mixture.

The amplification cycles are performed in the following manner: 30 to 40 cycles containing of:
94° C. for 10 seconds (denaturation),
60° C. for 1 minute 30 (hybridization),
78° C. for 1 minute 30 (elongation).

The whole series is followed by a single cycle at 78° C. for 15 minutes.

The accuracy to ±0.3° C. of the temperature indicated as well as their stability during the different parts of the cycles, are essential conditions for the production of maximal yields as well as insuring the absence of aspecific bands.

The optimal concentration of DNA is 100 to 300 ng in the case of genomic DNA extracted from cells (of patients or in culture, mammals or other species).

It is obvious that the preceding conditions represent optimal conditions for a final reaction mixture of 50 µl, and that these conditions may be modified, depending on the final volume of the reaction mixture.

The use of several different primer couples (or cocktails of couples) of the invention makes possible either the cross-detection of several types of the viruses of the HIV and/or SIV type, or the simultaneous detection of several genes of a given virus of the HIV and/or SIV type.

As examples of the preferred primer couples which can be used within the framework of the present invention, mention may be made of the following primer couples:

MMy1-MMy4, MMy2-MMy4, MMy1-MMy3, MMy18-MMy19, MMy4a-MMy28a, MMy28-MMy29a, MMy29-MMy30a, MMy30a-MMy31-MMy32a, in particular for the in vitro diagnosis of the infection of an individual by HIV-1 and/or HIV-2

MMy5-MMy8, MMy6-MMy8, MMy7-MMy8, MMy5-MMy7a, MMy6-MMy7a, MMy9-MMy11, MMy10-MMy11, MMy9-MMy10a, MMy26-MMy5a, MMy8a-MMy9a, MMy8a-MMy89, MMy89a-MMy9a, MMy15-MMy17, MMy15-MMy16a, MMy16-MMy17, MMy25-MMy27, MMy26-MMy27, in particular for the in vitro diagnosis of the infection of an individual by HIV-1, MMy20-MMy22, MMy20-MMy21a, MMy21-MMy22, MMy23-MMy24, MMy12-MMy14, MMy12-MMy13a, for the in vitro diagnosis of the infection of an individual by HIV-2.

The agent of polymerization used in the elongation step of the cycle is a thermostable DNA polymerase, in particular Taq polymerase, the amplifiose of the Appligene company or any thermostable DNA polymerase which is commercially available.

Generally speaking, the cycle of the method of in vitro diagnosis of the invention is repeated between 30 and 40 times.

Depending on the nucleotide primer couples used, the method of in vitro diagnosis of the invention also makes it possible to detect selectively the genes of the viruses of the HIV and/or SIV type present in the biological sample.

As examples of the primer couples which can be used for the above-mentioned method of diagnosis gene-per-gene of the invention are the following:

MMy1-MMy4, MMy2-MMy4, MMy1-MMy3, MMy4a-MMy28a for the gag gene,

MMy18-MMy19 for the vpr gene,

MMy5-MMy8, MMy6-MMy8, MMy7-MMy8, MMy5-MMy7a, MMy6-MMy7a, MMy26-MMy5a, MMy8a-MMy9a, MMy8a-MMy89, MMy89a-MMy9a for the env gene, MMy9-MMy11, MMy9-MMy10a, MMy10-MMy11 for the hef of HIV-1 Bru, HIV-1 Mal, and HIV-1 Eli gene, MMy15-MMy17, MMy15-MMy16a, MMy16-MMy17 for the vif of HIV-1 Bru, HIV-1 Mal, and HIV-1 Eli gene, MMy20-MMy22, MMy20-MMy21a, MMy21-MMy22 for the vif of HIV-2 ROD and SIV MAC gene MMy23-MMy24 for the vpx gene, MMy12-MMy14, MMy12-MMy13a, MMy13-MMy14 for the hef of HIV-2 ROD and SIV MAC gene, MMy25-MMy27, MMy26-MMy27 for the vpu gene, MMy28-MMy29a, MMy29-MMy30a, MMy30-MMy31a, MMy31-MMy32a for the pol gene.

However, the combinations between "S" and "AS" primers described above are not limiting and may be varied according to the wish of the user.

The sizes of the nucleotide fragments synthesized with the aid of the primer couples mentioned above as examples are shown in the following Tables I to XI: (the figures indicated in the Tables below represent the number of nucleotides in the fragments synthesized, and the "dashes" indicate that the primer couples tested do not make it possible to characterize the corresponding viral strains).

TABLE I

|  | gag | | gag | |
|---|---|---|---|---|
|  | MMy1–MMy3 | MMy1–MMy4 | MMy2–MMy4 | MMy4a–MMy28a |
| HIV1-BRU | 265 | 750 | 532 | 671 |
| HIV1-MAL | 282 | 785 | 556 | 671 |
| HIV1-ELI | 265 | 750 | 538 | 674 |
| HIV2-ROD | 354 | 845 | 544 | 663 |
| SIV | 343 | 844 | 544 | 668 |

TABLE II

|  | env | | env | |
|---|---|---|---|---|
|  | MMy5–MMy7a | MMy5–MMy8 | MMy6–MMy7a | MMy6–MMy8 |
| HIV1-BRU | 480 | 953 | 330 | 803 |
| HIV1-MAL | 471 | 944 | 321 | 794 |
| HIV1-ELI | 471 | 941 | 321 | 791 |
| HIV2-ROD | — | — | — | — |
| SIV | — | — | — | — |

TABLE III

|  | env | | env |
|---|---|---|---|
|  | MMy7–MMy8 | MMy26–MMy5a | MMy8a–MMy9a |
| HIV1-BRU | 498 | 691 | 1038 |
| HIV1-MAL | 498 | 691 | 1041 |
| HIV1-ELI | 495 | 679 | 1038 |
| HIV2-ROD | — | — | — |
| SIV | — | — | — |

TABLE IV

|  | env MMy8a–MMy89 | env MMy89a–MMy9a |
|---|---|---|
| HIV1-BRU | 411 | 646 |
| HIV1-MAL | 411 | 649 |
| HIV1-ELI | 411 | 646 |
| HIV2-ROD | — | — |
| SIV | — | — |

TABLE V

| | nef of HIV-1 Bru, HIV-1 Mal, and HIV-1 Eli | nef of HIV-1 Bru, HIV-1 Mal, and HIV-1 Eli | |
|---|---|---|---|
| | MMy9–MMy10a | MMy9–MMy11 | MMy10–MMy11 |
| HIV1-BRU | 293 | 660 | 388 |
| HIV1-MAL | 302 | 660 | 388 |
| HIV1-ELI | 296 | 663 | 388 |
| HIV2-ROD | — | — | — |
| SIV | — | — | — |

TABLE VI

| | nef of HIV-2 ROD and SIV MAC | | nef of HIV-2 ROD and SIV MAC |
|---|---|---|---|
| | MMy12–MMy13a | MMy12–MMy14 | MMy13–MMy14 |
| HIV1-BRU | — | — | — |
| HIV1-MAL | — | — | — |
| HIV1-ELI | — | — | — |
| HIV2-ROD | 400 | 792 | 415 |
| SIV | 400 | 755 | 378 |

TABLE VII

| | vif of HIV-1 Bru, HIV-1 Mal, and HIV-1 Eli | vif of HIV-1 Bru, HIV-1 Mal, and HIV-1 Eli | |
|---|---|---|---|
| | MMy15–MMy16a | MMy15–MMy17 | MMy16–MMy17 |
| HIV1-BRU | 333 | 603 | 293 |
| HIV1-MAL | 333 | 603 | 293 |
| HIV1-ELI | 333 | 603 | 293 |
| HIV2-ROD | — | — | — |
| SIV | — | — | — |

TABLE VIII

| | vpr | vif of HIV-2 ROD and SIV MAC | |
|---|---|---|---|
| | MMy18–MMy19 | MMy20–MMy21a | MMy20–MMy22 |
| HIV1-BRU | 281 | — | — |
| HIV1-MAL | 281 | — | — |
| HIV1-ELI | 281 | — | — |
| HIV2-ROD | 319 | 352 | 659 |
| SIV | 308 | 352 | 656 |

TABLE IX

| | vif of HIV-2 ROD and SIV MAC MMy21–MMy22 | vpx MMy23–MMy24 |
|---|---|---|
| HIV1-BRU | — | — |
| HIV1-MAL | — | — |
| HIV1-ELI | — | — |
| HIV2-ROD | 329 | 329 |
| SIV | 326 | 329 |

TABLE X

| | vpu | | pol |
|---|---|---|---|
| | MMy25-MMy27 | MMy26-MMy27 | MMy28-MMy29a |
| HIV1-BRU | 263 | 104 | 623 |
| HIV1-MAL | 263 | 101 | 584 |
| HIV1-ELI | 263 | 101 | 584 |
| HIV2-ROD | — | — | 666 |
| SIV | — | — | 712 |

TABLE XI

| | pol | | pol |
|---|---|---|---|
| | MMy29-MMy30a | MMy30-MMy31a | MMy31-MMy32a |
| HIV1-BRU | 742 | 869 | 826 |
| HIV1-MAL | 742 | 869 | 826 |
| HIV1-ELI | 742 | 869 | 826 |
| HIV2-ROD | 742 | 866 | 826 |
| SIV | 742 | 866 | 826 |

It is to be noted that owing to their arrangement on the genome, the primers used for amplification may be combined in a manner such that they can be used as probes, either after labelling with $^{32}P$ by means of a kinase, or for use in the procedure employing cold probes to check the specificity of the amplification band observed during an analysis by "Southern blot". In addition to the classical combination of the primers in order that a third oligonucleotide may serve as specific internal probe, the special case of the vif/vpr of HIV-1, Bru, HIV-1 Mal, and HIV-1 Eli and vif/vpx of HIV-2 ROD and SIV MAC genes due to the overlapping of these genes, which permits cross-detection, is to be noted. Furthermore, during an analysis of the amplified DNA by sequencing, these oligonucleotides may be used as specific primers for the DNA polymerase making possible a duplicate sequencing in each sense, hence a duplicate reading of the sequences, thus removing possible ambiguities in interpretation.

The object of the invention is also the primers such as those defined above, labelled in particular radioactively or enzymatically, as well as their use as nucleotide probes, in particular in the framework of the method of in vitro diagnosis such as described above.

The object of the invention is also oligoneotides such as those described above and containing sugars in the α-conformation. Such oligonucleotides exhibit the property of reversing the sense of the double helix formed with the matrix (strand of the genome of the virus), this double helix thus passing from the "S" state to the "AS" state.

The invention also relates to the oligonucleotides described above in which some nucleotides are methylated and/or contain one or more sulfur atoms, in particular at the adenine residues. Such oligonucleotides possess the property of increasing the stability of the double helix and consequently of hybridizing better with the DNA strand to be amplified.

The invention also relates to the oligonuceotides such as those described above existing in the so-called "modified base" form containing nucleotides to which chromphores are covalently grafted (planar aromatic molecules such as acridine orange), in particular according to the method described in the article by C. Hélène published in "la Vie des Sciences", compte-rendus, série générale, tome 4, No. 1, p. 17–37. Such oligonucleotides possess the property of being easily detectable, in particular by fluorescence.

The oligonucleotides of the invention can also be used for the implementation of a method of in vitro diagnosis of the infection of monkeys (macaque, mangabey monkey or green monkey) by the virus of the SIV type, this method duplicating the principal characteristics of that described above.

The object of the invention is also diagnostic kits for the implementation of the method of in vitro diagnosis mentioned above. As an example, a diagnostic kit of the present invention contains:

at least one oligonucleotide primer couple according to the invention, each couple consisting of a primer which hybridizes with one of the strands of the nucleic acid sequence to be detected, and a primer which hybridizes with the complementary strand of this latter under the conditions defined above, suitable reagents for the implementation of the cycle of amplification operations, in particular a DNA polymerase and the four different nucleoside triphosphates, and the reaction medium designated "10 x buffer" described above.

one (or more) probe which can be labelled, in particular by radioactivity, and which is capable of hybridizing specifically in the labelled or unlabelled form with the amplified nucleic acid sequence(s) to be detected.

The invention also relates to the use of the primers of the invention indicated above for the implementation of a procedure for the synthesis of proteins encoded in the nucleotide sequences amplified by means of these primers.

As an illustration, this procedure for the synthesis of proteins comprises the amplification of the nucleotide sequences of the genomes of the viruses of the HIV or SIV type (coding for a specific protein and, where appropriate, having undergone certain modifications of their nucleotides) by placing in contact the said sequences with at least one primer couple according to the invention under the conditions described above, followed by the translation of thes sequences thus amplified into proteins; this last step is carried out in particular by transformation of suitable host cells with the aid of vectors containing the said amplified sequences, and the recovery of the proteins in these host cells.

The invention also relates to the polypeptides derived from the translation of the nucleotide sequences (or primers) of the invention.

The object of the invention is also the use of the anti-sense oligonucleotide primers as antiviral agents in general, in particular to combat AIDS, as well as pharmaceutical compositions containing these anti-sense primers in combination with a pharmaceutically acceptable vehicle.

The invention also relates to the immunogenic compositions containing one or more translation products of the nucleotide sequences according to the invention, and/or one or more translation products of the nucleotide sequences amplified according to the procedures described above starting from primers defined according to the invention, these translation products being combined with a pharmaceutically acceptable vehicle.

The invention relates to the antibodies directed against one or more of the translation products described above (or, in other terms, capable of giving rise to an immunological reaction with one or more translation products of the nucleotide sequences according to the invention, or also one or more translation products of the amplified nucleotide sequences starting from primers defined according to the invention) and their use for the implementation of methods of in vitrodiagnosis of the infection of an individual by a virus of the HIV-1 and/or HIV-2 type, or of an animal by at least one of the three viruses (HIV-1, HIV-2, SIV) according to the procedures well-known to the person skilled in the art.

As an illustration, such a method of in vitro diagnosis according to the invention comprises the placing in contact of a biological sample (in particular serum), taken from a patient under study, with antibodies according to the invention, and the detection by means of any appropriate procedure (in particular with the aid of labelled anti-immunoglobulins) of the immunological complexes formed between the antigens of the viruses of the HIV or SIV type possibly present in the biological sample and the said antibodies.

The object of the invention is also kits for in vitro diagnosis containing antibodies according to the invention and, where appropriate, suitable reagents for the detection of the immunological complex formed by reaction between the said antibodies and the antigens of the HIV or SIV viruses.

The invention also relates to a procedure for the preparation of the polypeptides mentioned above, in particular those corresponding according to the universal genetic code to the nucleotide sequences (or primers) described above, this procedure being characterized in that, starting preferably from the C-terminal amino acid, successive amino acid residues are condensed successively one at a time in the required order, or amino acid residues and fragments previously formed and already containing several amino acid residues in the required order are condensed, or also several fragments thus prepared beforehand are condensed, it being understood that care will be taken to protect beforehand all of the reactive functions borne by these amino acid residues or fragments with the exception of the amine function of the one and the carboxyl function of the other, which normally must participate in the formation of the peptide bonds, in particular after activation of the carboxyl function according to the known methods of peptide synthesis and this is continued in a stepwise manner until the N-terminal amino acid is reached.

For example, recourse may be had to the procedure of peptide synthesis in homogeneous solution described by Houbenweyl in "Methoden der Organischen Chemie" (Methods of Organic Chemistry) edited by W. Wunsch, vol. 15-I and II, THIEME, STUTTGART, 1974, or to that of peptide synthesis on a solid phase described by R. D. Merrifield in "Solid Phase Peptide Synthesis" (J. Am. Chem. Soc., 45, 2149–2154).

The invention also relates to a procedure for the preparation of the nucleotide sequences (or primers) described above, this procedure comprising the following steps:

incubation of the genomic DNA, isolated from one of the viruses of the HIV or SIV type mentioned above, with DNAase I, then addition of EDTA and purification by extraction with the mixture phenol/chloroform/isoamyl alcohol (25/24/1), then by ether, treatment of the DNA thus extracted by Eco RI methylase in the presence of DTT, and purification by extraction as described above, incubation of the DNA thus purified with the 4 deoxy-nucleoside triphosphates dATP, dCTP, dGTP and dTTP in the presence of T4 DNA polymerase and DNA ligase of E.coli, then purification according to the method described above, the cloning of the nucleic acid thus obtained in a suitable vector and the recovery of the desired nucleic acid with the aid of a suitable probe.

A particularly useful procedure for the preparation of the nucleotide sequences of the invention comprises the following steps:

The synthesis of DNA by using the β-cyanoethyl phosphoramidite automated method described in Bioorganic Chemistry 4, 274–325 (1986), the cloning of the nucleic acid thus obtained in a suitable vector and the recovery of the nucleic acid by hybridization with a suitable probe.

Another procedure for the preparation of the nucleotide sequence of the invention comprises the following steps:

the set of chemically synthesized oligonucleotides, provided with various restriction sites at their ends, the sequences of which are compatible with the sequence of amino acids of the natural polypeptide according to the principle described in Proc. Natl. Acad. Sci. USA, 80, 7461–7465 (1983), the cloning of the nucleic acid thus obtained in a suitable vector and the recovery of the desired nucleic acid by hybridization with a suitable probe.

What is claimed is:

1. An oligonucleotide primer selected from the group consisting of a nucleotide sequence of the gag, vpr and pol genes of HIV-1 Bru, HIV-1 Mal, HIV-1 Eli, HIV-2 ROD, and SIV MAC; the nef, vif, and vpx genes of HIV-2 ROD and SIV MAC; and the env, nef, vif and vpu genes of HIV-1 Bru, HIV-1 Mal, and HIV-1 Eli; and nucleotide sequences complementary thereto, wherein said nucleotide sequence of gag is selected from the group considering of:
  MMy1: TGG CGC CCG AAC AGG GAC (SEQ ID No.:1) TGG CGC CTG AAC AGG GAC (SEQ ID No.:2)
  MMy2: GGC CAG GGG GAA AGA AAA A (SEQ ID No.:3) GGC CCG GCG GAA AGA AAA A (SEQ ID No.:4) GGC CCG GAG GAA AGA AAA A (SEQ ID No.5)
  MMy3: TGC CCA TAC AAA ATG TTT TA (SEQ ID No.:6) TGC CCA CAC TAT ATG TTT TA (SEQ ID No.:7)
  MMy4: TGC ATG GCT GCT TGA TG (SEQ ID No.:8) TGC ATA GCT GCC TGG TG (SEQ ID No.:9)
  MMy4B: CTT TGC ATG GCT GCT TGA TG (SEQ ID No.:10) CTC TGC ATA GCT GCT TGC TG (SEQ ID No.:11)
  MMy4Ba: CAT GCA GCA GCC ATG CAA AG (SEQ ID No.:12) CAC CAG GCA GCT ATG CAG AG (SEQ ID No.:13)
  MMy28: AGG GCT GTT GGA AAT GTG G (SEQ ID No.:14) AGG GCT GTT GGA AGT GTG G (SEQ ID No.:15)
  MMy28a: CCA CAT TTC CAG CAT CCC T (SEQ ID No.:16) CCA CAT TTC CAG CAG CCC T (SEQ ID No.:17) CCA CAT TTC CAG CAC CCC T (SEQ ID No.:18);

and wherein said nucleotide sequence of vpr is selected from the group consisting of:
  MMy18: GAT AGA TGG AAC AAG CCC CAG (SEQ ID No.:19)
  MMy19: TCC ATT TCT TGC TCT CCT CTG T (SEQ ID No.:20);

and wherein said nucleotides sequence of pool is selected from the group consisting of:
  MMy29: TAA AGC CAG GAA TGG ATG GCC CAA (SEQ ID No.:21) TAA AGC CAG GAA TGG ATG GAC CAA (SEQ ID No.:22)
  MMY29a. TTG GGC CAT CCA TTC CTG GCT TTA (SEQ ID No.:23) TTG GTC CAT CCA TTC CTG GCT TTA (SEQ ID No.:24)
  MMy30: TGG ACT GTC AAT GAC ATA CAG AA (SEQ ID No.:25) TGG ACT GTC AAT GAT ATA CAG AA (SEQ ID No.:26)
  MMy30a: TTC TGT ATG TCA TTG ACA GTC CA (SEQ ID No.:27) TTC TGT ATG TCA TTG ACT GTC CA (SEQ ID No.:28)
  MMy31: CAT GGG TAC CAG CAC ACA AAG G (SEQ ID No.:29)
  MMy31a: CCT TTG TGT GCT GGT ACC CAT G (SEQ ID No.:30)
  MMy32: TGG AAA GGT GAA GGG GCA GT (SEQ ID No.:31) TGG AAA GGT GAA GGA GCA GT (SEQ ID No.:32)
  MMy32a: ACT GCC CCT TCA CCT TTC CA (SEQ ID No.:33) ACT GCC CCT TCT CCT TTC CA (SEQ ID No.:34) ACT GCC CCT TCC CCT TTC CA (SEQ ID No.:35);

and wherein said nucleotide sequence of nef of HIV-2 ROD and SIV MAC is selected from the group consisting of:
  MMy12: AGA GAC TCT TGC GGG CGC GTG (SEQ ID No.:36)
  MMy13: ATA TAC TTA GAA AAG GAA GAA GG (SEQ ID No.:37)
  MMy13a: OCT TCT TCC TTT TCT AAG TAT AT (SEQ ID No.:38)
  MMy14: AGC TGA GAC AGC AGG GAC TTT CCA (SEQ ID No.:39);

and wherein said nucleotide sequence of vif of HIV-2 ROD and SIV MAC is selected from the group consisting of:
  MMy20: TAT GGA GGA GGA AAA GAG ATG GAT AGT (SEQ ID No.:40)
  MMy21: TAG CAC TTA TTT CCC TTG CTT T (SEQ ID No.:41)
  MMy21a: AAA GCA AGG GAA ATA AGT GCT A (SEQ ID No.:42)
  MMY22: CCC TTG TTC ATC ATG CCA GTA T (SEQ ID No.:43);

and wherein said nucleotide sequence of vpx is selected from the group consisting of:
  MMy23: ATG TCA GAT CCC AGG GAG A (SEQ ID No.:44)
  MMy24: CCT GGA GGG GGA GGA GGA GGA (SEQ ID No.:45):

and wherein the nucleotide sequences of the env are selected from the group consisting of:
  MMy5: CCA ATT CCC ATA CAT TAT TGT GCC CC (SEQ ID No.: 46)
  MMy5a: GGG GCA CAA TAA TGT ATG GGA ATT GG (SEQ ID No.: 47)
  MMy6: AAT GGC AGT CTA GCA GAA GAA GA (SEQ ID No.:48)
  MMy7: ATC CTC AGG AGG GGA CCC AGA AAT T (SEQ ID No.: 49)
  MMy7a: AAT TTC TGG GTC CCC TCC TGA GGA T (SEQ ID No.: 50)
  MMy8a: GTG CTT CCT GCT GCT CCC AAG AAC CC (SEQ ID No.: 51)
  MMy8a: GGG TTC TTG GGA GCA GCA GGA AGC AC (SEQ ID No.: 52)

MMy9: ATG GGT GGC AAG TGG TCA AAA AGT AG (SEQ ID No.: 53) ATG GGT GGC AAA TGG TCA AAA AGT AG (SEQ ID No.: 68)

MMy9a: CTA CTT TTT GAC CAC TTG CCA CCC AT (SEQ ID No.: 54)

MMy78: TAT TAA CAA GAG ATG GTG G (SEQ ID No.:55)

MMy89: CCA GCA AGA AAA GAA TGA A (SEQ ID No.:56)

MMy89: TTC ATT CTT TTC TTG CTG G (SEQ ID No.:57);

and wherein said nucleotide sequence of nef of HIV-1 HIV-1 Mal, and HIV-1 Eli is selected from the group consisting of:

MMy10: AAA AGA AAA GGG GGG ACT GGA (SEQ ID No.:58)

MMy10a: TCC AGT CCC CCC TTT TCT TTT (SEQ ID No.:59)

MMy11: AAA GTC CCC AGC GGA AAG TCC C (SEQ ID No.:60);

and wherein said nucleotide sequence of vif of HIV-1 Bru, HIV-1 Mal, and HIV-1 Eli is selected from the group consisting of:

MMy15: GAT TAT GGA AAA CAG ATG GCA GGT GAT (SEQ ID No.:61)

MMy16: GCA GAC CAA CTA ATT CAT CTG TA (SEQ ID No.:62)

MMy16a: TAC AGA TGA ATT AGT TGG TCT GC (SEQ ID No.:63)

MMy17: CTT AAG CTC CTC TAA AAG CTC TA (SEQ ID No.:64);

and wherein said nucleotide sequence of vpu is selected from the group consisting of:

MMy25: GTA AGT AGT ACA TGT AAT GCA ACC T (SEQ ID No.: 65)

MMy26: AGC AGA AGA CAG TGG CCA TGA GAG (SEQ ID No.:66)

MMy27: ACT ACA GAT CAT CAA TAT CCC AA (SEQ ID No.:67).

2. The oligonucleotide primer of claim 1, further comprising at least one of the 3' or 5' ends of said gag, vpr and pol genes of HIV-1 Bru, HIV-1 Mal, HIV-1 Eli, HIV-2 ROD, and SIV MAC; said nef, vif, and vpx genes of HIV-2 ROD and SIV MAC; and said env, nef, vif and vpu genes of HIV-1 Bru, HIV-1 Mal, and HIV-1 Eli an additional sequence of nucleotides identical to the nucleotides found 3' or 5', respectively, to the comparable region of said gag, vpr and pol genes of HIV-1 Bru, HIV-1 Mal, HIV-1 Eli, HIV-2 ROD, and SIV MAC; said nef, vif, and vpx genes of HIV-2 ROD and SIV MAC; and said env, nef, vif and vpu genes of HIV-1 Bru, HIV-1 Mal, and HIV-1 Eli within the complete sequence of the gag, vpr and pol genes of HIV-1 Bru, HIV-1 Mal, HIV-1 Eli, HIV-2 ROD, and SIV MAC; said nef, vif, and fpx genes of HIV-2 ROD and SIV MAC; and said env, nef, vif and vpu genes of HIV-1 Bru, HIV-1 Mal, and HIV-1 Eli, wherein the length of said primer with said additional sequence is not greater than 30 nucleotides and wherein the additional sequence is located immediately adjacent to the 3' or 5' end of the primer.

3. The oligonucleotide primer of claim 1, further comprising at least one of the 3' or 5' ends of said gag, vpr and pol genes of HIV-1 Bru, HIV-1 Mal, HIV-1 Eli, HIV-2 ROD, and SIV MAC; said nef, vif, and vpx genes of HIV-2 ROD and SIV MAC; and said env, nef, vif and vpu genes of HIV-1 Bru, HIV-1 Mal, and HIV-1 Eli an additional sequence of nucleotides identical to the nucleotides found 3' or 5', respectively, to the comparable region of said gag, vpr and pol genes of HIV-1 Bru, HIV-1 Mal, HIV-1 Eli, HIV-2 ROD, and SIV MAC; said nef, vif, and vpx genes of HIV-2 ROD and SIV MAC; and said env, nef, vif and vpu genes of HIV-1 Bru, HIV-1 Mal, and HIV-1 Eli within the complete sequence of the gag, vpr and pol genes of HIV-1 Bru, HIV-1 Mal, HIV-1 Eli, HIV-2 ROD, and SIV MAC; said nef, vif, and vpx genes of HIV-2 ROD and SIV MAC; and said env, nef, vif and vpu genes of HIV-1 Bru, HIV-1 Mal, and HIV-1 Eli, wherein the length of said primer with said additional sequence is not greater than 40 nucleotides and wherein the additional sequence is located immediately adjacent to the 3' or 5' end of the primer.

* * * * *

UNITED STATES PATENT AND TRADEMARK OFFICE
CERTIFICATE OF CORRECTION

| | | |
|---|---|---|
| PATENT NO. | : 7,078,516 B1 | |
| APPLICATION NO. | : 08/472928 | |
| DATED | : July 18, 2006 | |
| INVENTOR(S) | : Moncany et al. | |

It is certified that error appears in the above-identified patent and that said Letters Patent is hereby corrected as shown below:

On the Title page after (*) Notice:

"Subject to any disclaimer, the term of this patent is extended or adjusted under 35 U.S.C. 154(b) by 34 days."

should read

--Subject to any disclaimer, the term of this patent is extended or adjusted under 35 U.S.C. 154(b) by 0 days.--

Item (30) Foreign Application Priority Data should read:

--June 2, 1989 (FR) 8907354
September 20, 1989 (FR) 8912371
May 5, 1990 PCT/FR90/00393--

In claim 1, column 41, line 29, "No.5)" should read --No.:5)--.

In claim 1, column 41, line 54, "nucleotides" should read --nucleotide--.

In claim 1, column 41, line 54, "pool" should read --*pol*--.

In claim 1, column 41, line 59, "MMY29a." should read --MMy29a:--.

In claim 1, column 42, line 31, "OCT" should read --CCT--.

*In claim 1, column 42, line 44, "MMY22:" shuld read --MMy22:--

*In claim 1, column 42, line 51, "(SEQ ID No.:45):" should read --(SEQ ID No.:45);--.

*In claim 1, column 42, line 64, "MMy8a:" should read --MMy8:--.

*In claim 1, column 43, line 10, "MMy89:" should read --MMy89a:--.

*In claim 1, column 43, line 12, after "of HIV-1" insert --Bru,--.

UNITED STATES PATENT AND TRADEMARK OFFICE
CERTIFICATE OF CORRECTION

PATENT NO. : 7,078,516 B1
APPLICATION NO. : 08/472928
DATED : July 18, 2006
INVENTOR(S) : Moncany et al.

It is certified that error appears in the above-identified patent and that said Letters Patent is hereby corrected as shown below:

In claim 2, column 44, line 13, "fpx" should read --*vpx*--.

Signed and Sealed this

Twelfth Day of December, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,078,516 B1 | Page 1 of 2 |
| APPLICATION NO. | : 08/472928 | |
| DATED | : July 18, 2006 | |
| INVENTOR(S) | : Moncany et al. | |

It is certified that error appears in the above-identified patent and that said Letters Patent is hereby corrected as shown below:

On the Title Page
Item (45) Date of Patent

"Jul. 18, 2006"

should read:

Item --(45) *Jul. 18, 2006--

On the Title Page, insert the following text immediately above Item "(21) Appl. No.: 08/472,928":

--This patent is subject to a terminal disclaimer.--

Item (62) Related U.S. Application Data

"Division of application No. 08/160,465, filed on Dec. 2, 1993, now Pat. No. 5,688,637, which is a continuation of application No. 07/820,599, filed on Jan. 21, 1992, now abandoned."

should read:

--Division of application No. 08/160,465, filed on Dec. 2, 1993, now Pat. No. 5,688,637, which is a continuation of application No. 07/820,599, which entered the national stage on Jan. 21, 1992, now abandoned, and which is a national stage application of International Application No. PCT/FR90/00393, filed on June 5, 1990.--

UNITED STATES PATENT AND TRADEMARK OFFICE
CERTIFICATE OF CORRECTION

PATENT NO. : 7,078,516 B1
APPLICATION NO. : 08/472928
DATED : July 18, 2006
INVENTOR(S) : Moncany et al.

It is certified that error appears in the above-identified patent and that said Letters Patent is hereby corrected as shown below:

On the Title Page
Item (30) Foreign Application Priority Data

"June 2, 1989      FR    89 07354
September 20, 1989  FR    89 12371
May 5, 1990              PCT/FR90/00393"

should read:

--June 2, 1989     FR    89 07354
September 20, 1989  FR    89 12371--

In claim 1, col. 41, line 22, "considering" should read --consisting--.

Signed and Sealed this

Third Day of November, 2009

David J. Kappos
*Director of the United States Patent and Trademark Office*